(12) United States Patent  
Michaud et al.

(10) Patent No.: US 10,106,645 B2  
(45) Date of Patent: Oct. 23, 2018

(54) HYDROCARBON POLYMERS HAVING TWO AZLACTONE END GROUPS

(71) Applicants: BOSTIK SA, La Plaine Saint Denis (FR); Universite de Rennes I, Rennes (FR); Centre National de la Recherche Scientifique, Paris (FR)

(72) Inventors: Guillaume Michaud, Compiegne (FR); Frederic Simon, Pont L'Eveque (FR); Stephane Fouquay, Mont Saint-Aignan (FR); Elise Vanbiervliet, Rennes (FR); Sophie Guillaume, Vitre (FR); Jean-Francois Carpentier, Acigne (FR)

(73) Assignees: BOSTIK SA, La Plaine Saint Denis (FR); Universite de Rennes I, Rennes (FR); Centre National de la Recherche Scientifique, Paris (FR)

(*) Notice: Subject to any disclaimer, the term of this patent is extended or adjusted under 35 U.S.C. 154(b) by 0 days.

(21) Appl. No.: 15/653,143

(22) Filed: Jul. 18, 2017

(65) Prior Publication Data

US 2018/0022864 A1 Jan. 25, 2018

(30) Foreign Application Priority Data

Jul. 19, 2016 (FR) ...................... 16 56864

(51) Int. Cl.
*C08F 2/00* (2006.01)
*C08F 210/00* (2006.01)
(Continued)

(52) U.S. Cl.
CPC ........... *C08G 61/08* (2013.01); *C07D 263/42* (2013.01); *B01J 2231/54* (2013.01);
(Continued)

(58) Field of Classification Search
CPC ............ C08G 61/08; C08G 2261/3322; C08G 2261/418; C07D 263/42; B01J 2231/54; B01J 2231/821
(Continued)

(56) References Cited

U.S. PATENT DOCUMENTS 6,759,484 B1 * 7/2004 Murayama ............... C08F 20/38
524/114
6,888,018 B2 5/2005 Morita et al.
(Continued)

FOREIGN PATENT DOCUMENTS

| EP | 0 128 731 | * 12/1984 |
| EP | 0128731 A1 | 12/1984 |
| EP | 1334977 A1 | 8/2003 |
| WO | 2013151739 A1 | 10/2013 |

OTHER PUBLICATIONS

Search Report for FR1656864 dated Mar. 27, 2017.
Lapinte, V. et al., "Synthesis and Ring-Opening Metathesis Polymerization (ROMP) Reactivity of endo-and exo-Norbornenylazlactone Using Ruthenium Catalyst," Macromolecular Chemistry and Physics, Apr. 1, 2004, vol. 205, No. 6, pp. 824-833.

*Primary Examiner* — William K Cheung
(74) *Attorney, Agent, or Firm* — Millen, White, Zelano and Branigan, P.C.

(57) ABSTRACT

1) Hydrocarbon polymer having two azlactone end groups

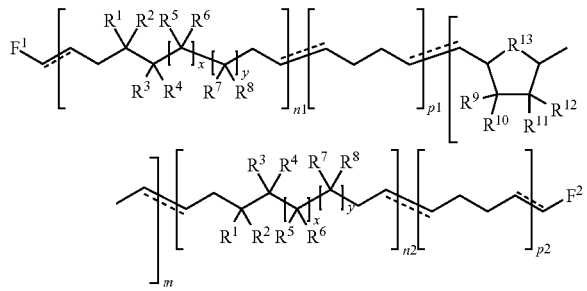

$F^1$ is formula (IIa) and $F^2$ is formula (IIb):

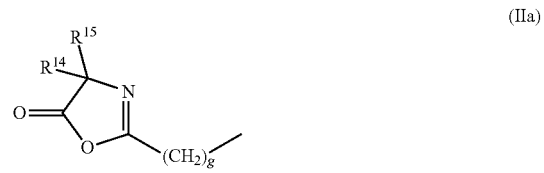

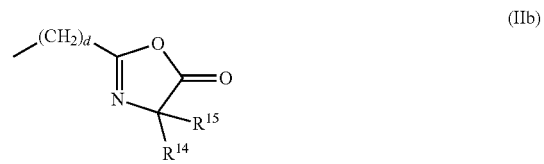

g and d are 0, 1, 2 or 3;
$R^{14}$ and $R^{15}$ are $C_1$-$C_4$ or a cyclohexyl radical;
$R^1$ to $R^{12}$ represents hydrogen or alkyl with 1 to 22 carbon atoms;
x and y are integers, x+y is 0 to 2;
$R^{13}$ is oxygen or sulphur or divalent —$CH_2$—
n1, n2, m, p1 and p2 are an integer or equal to 0 and such that the molecular weight Mn of the polymer of formula (I) is between 400 and 100 000 g/mol; a process for preparation of the polymer; and use as adhesive in mixture with an amino compound with at least two amine groups.

9 Claims, No Drawings

(51) Int. Cl.
  *C08G 61/08* (2006.01)
  *C07D 263/42* (2006.01)
(52) U.S. Cl.
  CPC . *B01J 2531/821* (2013.01); *C08G 2261/3322* (2013.01); *C08G 2261/418* (2013.01)
(58) Field of Classification Search
  USPC .................................................. 526/217, 348
  See application file for complete search history.

(56) References Cited

U.S. PATENT DOCUMENTS

| | | |
|---|---|---|
| 9,217,050 B2 | 12/2015 | Fornof et al. |
| 2004/0015002 A1 | 1/2004 | Morita et al. |
| 2006/0173145 A1 | 8/2006 | Pawlow et al. |
| 2015/0232596 A1 | 8/2015 | Fornof et al. |

\* cited by examiner

HYDROCARBON POLYMERS HAVING TWO AZLACTONE END GROUPS

A subject matter of the present invention is hydrocarbon polymers comprising two azlactone (also known as oxazolone) end groups, their preparation and their use as adhesive.

Polyurethanes are widely used in the field of adhesives, due to the versatility of their properties, rendered possible by their very high number of structural forms.

Polyurethanes are conventionally synthesized by reaction between a diol and a diisocyanate. Diisocyanates are toxic compounds as such and are generally obtained from phosgene, itself very toxic by inhalation or by contact. The manufacturing process used industrially generally employs the reaction of an amine with an excess of phosgene in order to form an isocyanate.

The search for alternatives to the synthesis of polyurethanes without using isocyanate (or NIPU for Non Isocyanate PolyUrethane) thus represents a major challenge for the adhesives industry.

Mention may be made, as example of such an approach, of Patent Application WO 2014/091173 on behalf of Bostik and the CNRS, which describes hydrocarbon polymers comprising two end groups having a (2-oxo-1,3-dioxolan-4-yl) ending which are capable of being obtained by ring-opening metathesis polymerization starting from at least one cyclic cycloolefin, at least one non-cyclic unsaturated chain transfer agent comprising an (2-oxo-1,3-dioxolan-4-yl) end group and at least one metathesis catalyst. These polymers can subsequently react with a (poly)amine to form polyurethanes, without employing isocyanate, which can advantageously be used to formulate coating, mastic or adhesive compositions. However, this reaction is relatively lengthy and remains to be improved.

This is why it can also be envisaged, as an alternative to this approach, to envisage the search for novel families of compounds having adhesive properties which do not require the use of isocyanates for their preparation and which are capable of exhibiting the same versatility of properties as that of the polyurethanes.

There are thus known, by Patent Application EP 0 105 665, compounds having azlactone end groups which are capable of reacting by opening of the azlactone ring, in the presence of reactants having a nucleophilic group, such as amines, in order to form thermoplastic and thermoset polyamides of use in particular as adhesives.

One aim of the present invention is to provide novel compounds having azlactone end groups which are capable of offering advantageous properties in the field of adhesives, for example in terms of mechanical properties of the adhesive seal and in particular of its viscoelastic properties.

Another aim of the present invention is to provide polymers having azlactone end groups and having a saturated or unsaturated main hydrocarbon chain which are capable of being obtained with a high yield.

Thus, the present invention relates to a hydrocarbon polymer comprising two azlactone (also known as oxazolone) end groups, said hydrocarbon polymer having the formula (I):

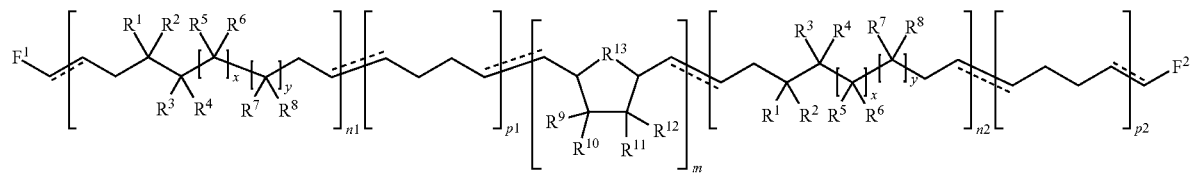

(I)

in which:
$F^1$ represents a radical of formula (IIa) and $F^2$ represents a radical of formula (IIb):

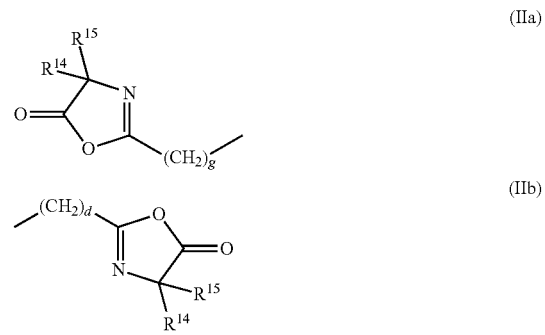

in which:
g and d, which are identical or different, represent an integer equal to 0, 1, 2 or 3;

$R^{14}$ and $R^{15}$, which are identical or different, represent a hydrogen atom or an aromatic or linear or branched aliphatic hydrocarbon group comprising from 1 to 20 carbon atoms which can be interrupted by one or more oxygen or sulphur atoms; in addition, the $R^{14}$ and $R^{15}$ groups can form, with the carbon atom to which they are connected, a hydrocarbon ring comprising from 4 to 10 ring members and optionally one or more heteroatoms chosen from oxygen and sulphur;

each carbon—carbon bond of the main chain of the polymer, denoted ------, represents a double bond or a single bond, in accordance with the valency rules of organic chemistry;

$R^1$, $R^2$, $R^3$, $R^4$, $R^5$, $R^6$, $R^7$ and $R^8$, which are identical or different, represent:
a hydrogen or halogen atom; or
a radical comprising from 1 to 22 carbon atoms chosen from alkyl, alkenyl, alkoxycarbonyl, alkenyloxycarbonyl, alkylcarbonyloxy or alkenylcarbonyloxy, it being possible for the hydrocarbon chain of the said radical to be optionally interrupted by at least one oxygen atom or one sulphur atom; in addition:
at least one of the $R^1$ to $R^8$ groups can form, with at least one other of the $R^1$ to $R^8$ groups and with the carbon atom or atoms to which the said groups are connected, a saturated or unsaturated hydrocarbon ring or heterocycle which is optionally substituted and which comprises from 3 to 10 ring members; and at least one of the pairs $(R^1, R^2)$, $(R^3, R^4)$, $(R^5, R^6)$ and $(R^7, R^8)$ can form, with the carbon atom to which the said pair is connected, a carbonyl C=O group or a group of 2 carbon atoms connected by a double bond: C=C, the other carbon atom of which carries 2 substituents chosen from a hydrogen atom or a $C_1$-$C_4$ alkyl radical;

x and y are integers, which are identical or different, within a range extending from 0 to 6, the sum x+y being within a range extending from 0 to 6;

$R^9$, $R^{10}$, $R^{11}$ and $R^{12}$, which are identical or different, represent:
  a hydrogen or halogen atom; or
  a radical comprising from 1 to 22 carbon atoms which is chosen from alkyl, alkenyl, alkoxycarbonyl, alkenyloxycarbonyl, alkylcarbonyloxy, alkenylcarbonyloxy or alkylcarbonyloxyalkyl, it being possible for the hydrocarbon chain of the said radical to be optionally interrupted by at least one oxygen atom or one sulphur atom; in addition:
  at least one of the $R^9$ to $R^{12}$ groups can form, with at least one other of the $R^9$ to $R^{12}$ groups and with the carbon atom or atoms to which the said groups are connected, a saturated or unsaturated hydrocarbon ring or heterocycle which is optionally substituted and which comprises from 3 to 10 ring members; and
  at least one of the pairs $(R^9, R^{10})$ and $(R^{11}, R^{12})$ can form, with the carbon atom to which the said pair is connected, a group of 2 carbon atoms connected by a double bond: C=C, the other carbon atom of which carries 2 substituents chosen from a hydrogen atom or a $C_1$-$C_4$ alkyl radical; and
  the carbon atom carrying one of the groups of the pair $(R^9, R^{10})$ can be connected to the carbon atom carrying one of the groups of the pair $(R^{11}, R^{12})$ by a double bond, it being understood that, in accordance with the valency rules, just one of the groups of each of these 2 pairs is then present;

$R^{13}$ represents:
  an oxygen or sulphur atom, or
  a divalent —$CH_2$—, —C(=O)— or —$NR^0$— radical in which $R^0$ is an alkyl or alkenyl radical comprising from 1 to 22 carbon atoms;

n1 and n2, which are identical or different, are each an integer or equal to 0, the sum of which is denoted by n;

m is an integer or equal to 0;

p1 and p2, which are identical or different, are each an integer or equal to 0, the sum p1+p2 of which adheres to the equation:

$$p1+p2=q\times(z+1)$$

in which:
  q is an integer or equal to 0; and
  z is an integer ranging from 1 to 5; and
  n1, n2, m, p1 and p2 additionally being such that the number-average molecular weight Mn of the polymer of formula (I) is within a range extending from 400 to 100 000 g/mol and its polydispersity index is within a range extending from 1.0 to 3.0.

The various groups, radicals and letters which are included in the formula (I) and which are defined above retain the same definitions throughout the present text, unless otherwise indicated.

The following alternative forms of the polymer of formula (I), taken individually or in combination, are particularly preferred:
  the $R^{14}$ and $R^{15}$ radicals included in the definition of $F^1$ and $F^2$ represent a $C_1$-$C_4$ alkyl radical, preferably a linear $C_1$-$C_4$ alkyl radical, or else form, with the carbon atom to which they are connected, a cyclohexyl radical;
  g and d included in the definition of $F^1$ and $F^2$ represent 0 or 1, and are preferably identical;
  $R^1$, $R^2$, $R^3$, $R^4$, $R^5$, $R^6$, $R^7$ and $R^8$ represent a hydrogen atom or an alkyl radical comprising from 1 to 14 carbon atoms and more preferably from 1 to 8;
  the integers x and y are within a range extending from 0 to 2, the sum x+y being within a range extending from 0 to 2;
  x is equal to 1 and y is equal to 1;
  $R^9$, $R^{10}$, $R^{11}$ and $R^{12}$ represent a hydrogen atom or a radical, the hydrocarbon part of which comprises from 1 to 14 carbon atoms and more preferably still from 1 to 8;
  $R^{13}$ represents the divalent —$CH_2$— radical;
  z is an integer equal to 1 or 2; and/or
  the number-average molecular weight Mn is within a range extending from 3000 to 50 000 g/mol, more particularly from 5000 to 30 000 g/mol, and the polydispersity index is within a range extending from 1.4 to 2.0.

The main chain of the polymer of formula (I) can thus comprise just one repeat unit chosen from:
  the repeat unit repeated p1+p2 times, or
  the repeat unit repeated n1+n2 times, or also
  the repeat unit repeated m times.

It can also comprise 2 units chosen from any two of the 3 units identified above and it can also comprise these 3 units; it is then understood that the distribution of the said units over the said main chain is random and that the polymer of formula (I) is thus a random polymer.

As is apparent above, the $F^1$ and $F^2$ end groups are generally symmetrical with respect to the main chain, that is to say that they substantially correspond, with the exception of the indices g and d.

The term "end group" is understood to mean a group located at one of the 2 extremities of the main chain of the polymer, which chain consists of one or more repeat units.

The polydispersity index (or PDI) is defined as the ratio Mw/Mn, that is to say the ratio of the weight-average molecular weight to the number-average molecular weight of the polymer.

In the present text, the two average molecular weights Mn and Mw are measured by size exclusion chromatography (or SEC), which is also denoted by the term of gel permeation chromatography (or GPC). The calibration carried out is usually a PEG (PolyEthylene Glycol) or PS (PolyStyrene), preferably PS, calibration.

If g=0 or d=0, then there is no —($CH_2$)— radical in the $F^1$ and $F^2$ groups of the formulae (IIa) and (IIb). In other words, the: —($CH_2$)$_g$— or —($CH_2$)$_d$— radical is replaced with a single bond.

When one of the indices n1, n2, p1, p2, m, x or y which applies to an assembly of two square brackets is equal to zero, this means that there is no group between the square brackets to which this index applies. Thus, for example, the group:

represents a single bond: —, and the group:

represents a double bond. =.

The polymers of formula (I) according to the invention are particularly homogeneous and temperature stable.

They can form, after a polyaddition reaction at a temperature of less than 80° C. with a primary and/or secondary polyamine, a polyamide which can constitute an adhesive seal.

The adhesive seal thus formed exhibits high cohesive values, in particular of greater than 2 MPa. Such cohesive values make possible use of the said polymer as adhesive, for example as leaktightness seal on an ordinary support (concrete, glass, marble), in the building industry, or also for the adhesive bonding of glazings in the motor vehicle and shipbuilding industries.

The polymers of formula (I) according to the invention are solid or liquid at ambient temperature (i.e. approximately 20° C.).

According to a preferred alternative form of the polymer according to the invention, when m is non-zero, when p1 and p2 are non-zero and when n1 and n2 are each equal to 0 (corresponding to the presence in the main chain of the polymer of the 2 repeat units alone repeated respectively p1+p2 times and m times), then the ratio:

$$m/(p1+p2+m)$$

is within the interval ranging from 30 to 70% and more preferably is equal to approximately 50%.

According to a second alternative of this same preferred alternative form, when m is equal to 0, when p1 and p2 are non-zero and when the sum n1+n2 is non-zero (corresponding to the presence in the main chain of the polymer of the 2 repeat units alone repeated respectively p1+p2 times and n1+n2 times), then at least one of the $R^1$, $R^2$, $R^3$, $R^4$, $R^5$, $R^6$, $R^7$ and $R^8$ groups is other than a hydrogen atom, and the ratio:

$$(n1+n2)/(p1+p2+n1+n2)$$

is within the interval ranging from 30 to 70% and more preferably is equal to approximately 50%.

According to a third alternative of this same preferred alternative form, when m is other than 0, when p1 and p2 are each equal to 0, when the sum n1+n2 is non-zero (corresponding to the presence in the main chain of the polymer of the 2 repeat units alone repeated respectively m times and n1+n2 times) and when each of the $R^1$, $R^2$, $R^3$, $R^4$, $R^5$, $R^6$, $R^7$ and $R^8$ groups is a hydrogen atom, then the ratio:

$$m/(m+n1+n2)$$

is within the interval ranging from 30 to 70% and more preferably is equal to approximately 50%.

According to yet a fourth alternative of the said preferred alternative form, when m is non-zero, when p1 and p2 are non-zero and when the sum n1+n2 is non-zero (corresponding to the presence in the main chain of the polymer of the 3 repeat units) and when each of the $R^1$, $R^2$, $R^3$, $R^4$, $R^5$, $R^6$, $R^7$ and $R^8$ groups is a hydrogen atom, then the ratio:

$$m/(p1+p2+n1+n2+m)$$

is within the interval ranging from 30 to 70% and more preferably is equal to approximately 50%.

According to yet a fifth alternative of the said preferred alternative form, when m is non-zero, when p1 and p2 are non-zero and when the sum n1+n2 is non-zero (corresponding to the presence in the main chain of the polymer of the 3 repeat units) and when at least one of the $R^1$, $R^2$, $R^3$, $R^4$, $R^5$, $R^6$, $R^7$ and $R^8$ groups is other than a hydrogen atom, then the ratio:

$$(m+n1+n2)/(p1+p2+n1+n2+m)$$

is within the interval ranging from 30 to 70% and more preferably is equal to approximately 50%.

In accordance with the 5 alternatives of the said preferred alternative form, the polymer of formula (I) is generally provided in the form of a viscous liquid and is characterized by a Brookfield viscosity at 23° C. ranging from 1 mPa·s to 500 Pa·s, preferably from 1 to 150 Pa·s and more preferably still from 1 to 50 Pa·s. It is then advantageously easy to employ and can be combined with an additional constituent, such as a tackifying resin or a filler, in order to form an adhesive composition.

When the polymer according to the invention is solid at ambient temperature, it is thermoplastic, that is to say deformable and meltable under hot conditions (i.e. at a temperature greater than ambient temperature). It can thus be used, as a mixture with a polyamine at the time of use, as two-component adhesive applied to the interface of substrates to be assembled at their faying surface.

According to one embodiment of the invention, all the ===== bonds of the formula (I) are carbon-carbon double bonds and the formula (I) then becomes the following formula (I'):

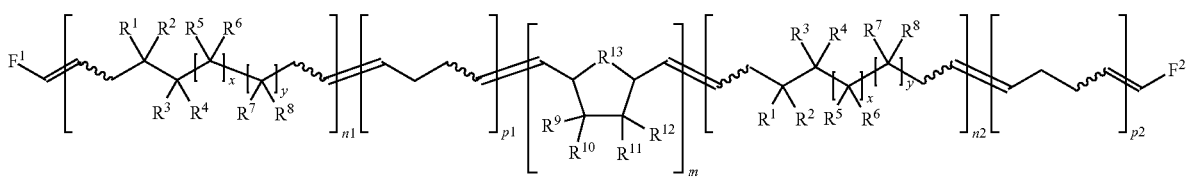

(I')

in which x, y, n1, n2, m, p1, p2, $F^1$, $F^2$, $R^1$, $R^2$, $R^3$, $R^4$, $R^5$, $R^6$, $R^7$, $R^8$, $R^9$, $R^{10}$, $R^{11}$, $R^{12}$ and $R^{13}$ have the meanings given above and the ∿∿∿ bond is a bond geometrically oriented on one side or the other with respect to the double bond (cis or trans).

Each of the double bonds of the polymer of formula (I') is geometrically cis or trans oriented; preferably is of cis orientation. The geometric isomers of the polymer of formula (I') are generally present in variable proportions, with most often a majority of double bonds oriented cis (Z) and preferably all oriented cis (Z). It is also possible according to the invention to obtain just one of the geometric isomers, according to the reaction conditions and in particular according to the nature of the catalyst used.

According to another embodiment of the invention, all the ----- bonds of the formula (I) are carbon-carbon single bonds and the formula (I) then becomes the formula (IH) below:

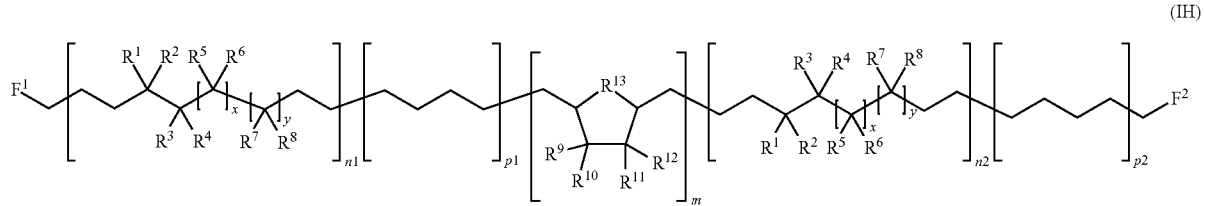

(IH)

in which x, y, n1, n2, m, p1, p2, $F^1$, $F^2$, $R^1$, $R^2$, $R^3$, $R^4$, $R^5$, $R^6$, $R^7$, $R^8$, $R^9$, $R^{10}$, $R^{11}$, $R^{12}$ and $R^{13}$ have the meanings given above.

The formula (IH) illustrates the case where the main chain of the polymer of formula (I) is saturated, that is to say comprises only saturated bonds.

In this case, preferably, x is equal to 1 and y is equal to 1.

The polymer of formula (IH) can, for example, result from the hydrogenation of the unsaturated polymer of formula (I').

According to one embodiment of the polymer of formula (I) according to the invention, m, p1 and p2 are each equal to 0, the polymer being of following formula (II):

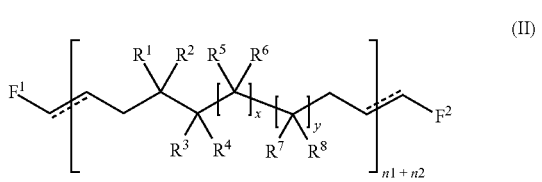

(II)

in which x, y, n1, n2, $F^1$, $F^2$, $R^1$, $R^2$, $R^3$, $R^4$, $R^5$, $R^6$, $R^7$ and $R^8$ have the meanings given above.

Particularly preferably, x is equal to 1 and y is equal to 1.

According to a particularly preferred form of this embodiment, all the ----- bonds of the formula (II) are carbon-carbon double bonds and the formula (II) then becomes the following formula (II'):

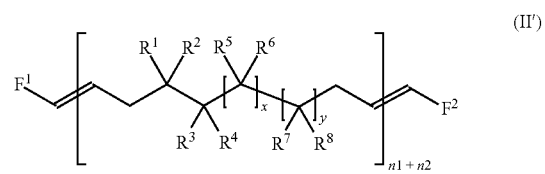

(II')

The formulae (II) and (II') illustrate the case where the main chain of the polymer of formula (I) comprises just one repeat unit, corresponding to that which is repeated n1+n2 times.

According to another embodiment of the polymer of formula (I) according to the invention, n1 and n2 are each equal to 0, the polymer being of following formula (III):

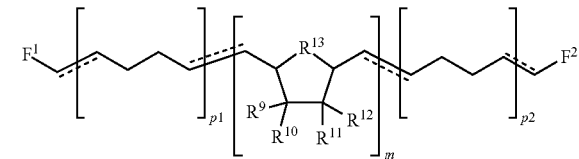

(III)

in which m, p1, p2, $F^1$, $F^2$, $R^9$, $R^{10}$, $R^{11}$, $R^{12}$ and $R^{13}$ have the meanings given above.

According to a particularly preferred form of this embodiment, all the ----- bonds of the formula (III) are carbon-carbon double bonds and the formula (III) then becomes the following formula (III'):

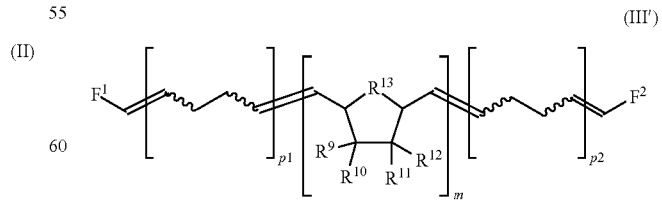

(III')

The formulae (III) and (III') illustrate the case where the main chain of the polymer of formula (I) comprises two repeat units, corresponding to those which are repeated respectively (p1+p2) times and m times.

As regards the azlactone end groups of the polymer according to the invention, preferably $R^{14}$ and $R^{15}$ each represent a methyl radical. In this case, $F^1$ and $F^2$ are identical and represent either the radical:

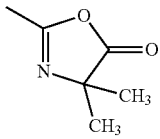

or else the radical:

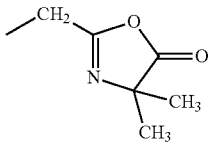

According to another preferred alternative form, $R^{14}$ and $R^{15}$ form, with the carbon atom to which they are connected, a cyclohexyl. In this case, $F^1$ and $F^2$ are identical and represent the radical:

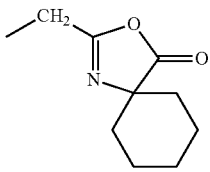

The invention also relates to a process for the preparation of a hydrocarbon polymer comprising two azlactone end groups of formula (I) according to the invention, the said process comprising at least one ring-opening metathesis polymerization (ROMP) reaction, in the presence:
(a) of a metathesis catalyst;
(b) of a chain transfer agent (also denoted below by CTA) comprising 2 azlactone groups, of following formula (B):

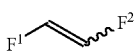
(B)

in which:
$F^1$ and $F^2$ are as defined above;
the ⁓ bond is a bond geometrically oriented on one side or the other with respect to the double bond (cis or trans); and
(c) of at least one compound C chosen from:
the compound of formula (C1):

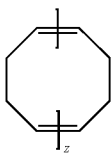
(C1)

in which z is as defined above;
the compound of formula (C2):

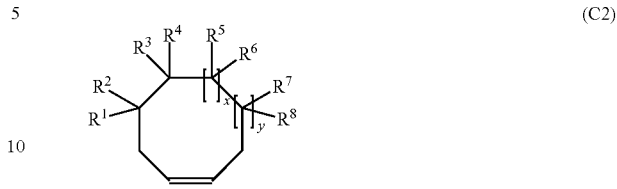
(C2)

in which $R^1$, $R^2$, $R^3$, $R^4$, $R^5$, $R^6$, $R^7$, $R^8$, x and y are as defined above; and
the compound of formula (C3):

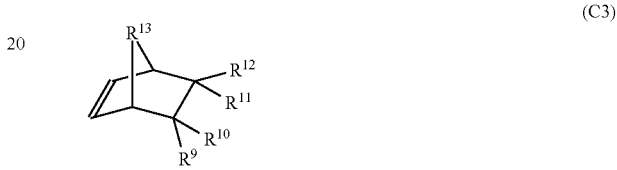
(C3)

in which $R^9$, $R^{10}$, $R^{11}$, $R^{12}$ and $R^{13}$ are as defined above;
the said polymerization reaction being in addition carried out:
for a time ranging from 2 to 24 hours and at a temperature within an interval from 20 to 70° C.; and
with a ratio r, equal to the ratio of the number of moles of the said CTA to the total number of moles of the compound C, within an interval ranging from 0.0010 to 1.0.

In the definition of the preparation process given above, it is clearly understood that the indefinite article "a" or "an" as it relates to a reactant or to the catalyst employed should be interpreted as meaning "at least one", that is to say "one or more". In particular, the said process can employ just one or several compound(s) C having either the same formula or else a different formula, preferably of different formula. When the process employs several compound(s) C, the denominator of the ratio r defined above is the sum of the total number of moles of the compounds C employed.

According to a preferred alternative form of the said process, just one compound C is employed, corresponding to the formula (C2).

According to another preferred alternative form of the said process, two compounds C are employed, one corresponding to the formula (C1) and the other to the formula (C3).

The duration and the temperature of the reaction depend generally on its operating conditions, in particular on the nature of the solvent used and especially on the content of catalytic filler. A person skilled in the art is in a position to adjust them as a function of the circumstances.

Thus, preferably, the duration of the polymerization reaction ranges from 2 to 10 hours and the ratio r defined above is within an interval ranging from 0.0010 to 0.3.

(a) Metathesis Catalyst:

The metathesis catalyst is preferably a ruthenium-comprising catalyst and more preferably still a Grubbs catalyst.

Such a catalyst is generally a commercial product.

The metathesis catalyst is generally a transition metal catalyst, including in particular a ruthenium-comprising catalyst, generally in the form of ruthenium complex(es), such as a ruthenium-carbene complex.

The term "Grubbs catalyst" is generally understood to mean, according to the invention, a $1^{st}$ or $2^{nd}$ generation Grubbs catalyst but also any other catalyst of Grubbs type (of ruthenium-carbene type) or Hoveyda-Grubbs type accessible to a person skilled in the art, such as, for example, the substituted Grubbs catalysts described in U.S. Pat. No. 5,849,851.

(b) CTA of Formula (B):

The CTA of formula (B) can be prepared from unsaturated dicarboxylic acids comprising from 4 to 18 carbon atoms and from a natural or synthetic α-amino acid according to the procedure described below:

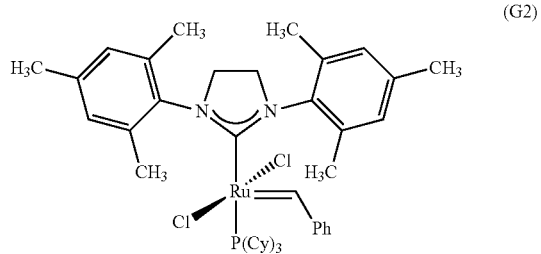

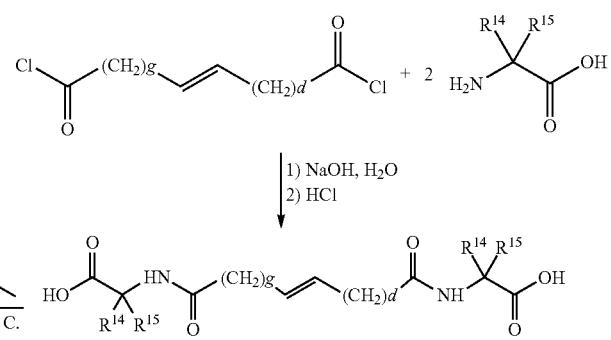

CTA of formula (B)

A $1^{st}$ generation Grubbs catalyst is generally of formula (G1):

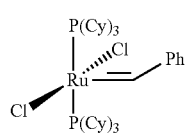

in which Ph is phenyl, Cy is cyclohexyl and the $P(Cy)_3$ group is a tricyclohexylphosphine group.

The IUPAC name of this compound is: benzylidenebis(tricyclohexylphosphine)dichlororuthenium (of CAS number 172222-30-9). Such a catalyst is available in particular from Aldrich.

A $2^{nd}$ generation (or G2) Grubbs catalyst is generally of formula (G2):

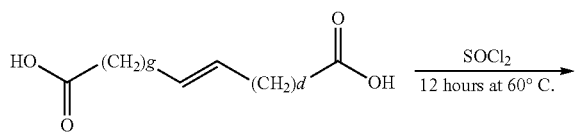

in which Ph is phenyl and Cy is cyclohexyl.

The IUPAC name of the second generation of this catalyst is benzylidene[1,3-bis(2,4,6-trimethylphenyl)-2-imidazolidinylidene]dichloro(tricyclohexylphosphine)ruthenium (of CAS number 246047-72-3). This catalyst is also available from Aldrich.

Mention may be made, as examples of natural α-amino acid capable of being employed in this procedure, of: alanine, valine, isoleucine, leucine, methionine or phenylalanine.

Synthetic α-amino acids monosubstituted in the α position and synthetic α-amino acids bisubstituted in the a position can be prepared according to Ooi, T. and Maruoka, K., Angew. Chem. Int. Ed., 2007, 46, 4222, and Ooi, T. and Maruoka, K., Aldrichimica Acta, 2007, 40, 77.

The α-amino acid in which $R^{14}$ and $R^{15}$ form, with the carbon atom to which they are connected, a cyclohexyl radical can be prepared from cyclohexanone according to the procedure described in Aboul-Enein, M. N., El-Azzouny, A. A., Abdallah, N. A. and Makhlouf, A. A., Egyptian Journal of Chemistry, 1991, vol. 34, #6, pp. 549-558.

In accordance with a preferred alternative form of the invention, the $R^{14}$ and $R^{15}$ groups included in the formula (B) of the CTA each represent a methyl radical. In this case, $F^1$ and $F^2$ are identical and the CTA of formula (B) is advantageously:

the compound of formula:

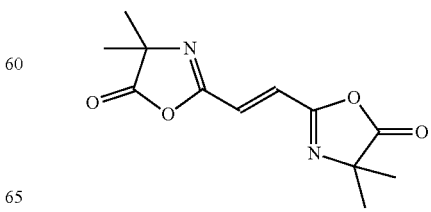

denoted below as CTA AzI₂; or else
the compound of formula:

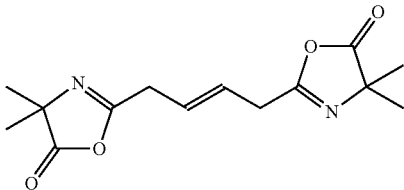

denoted below as CTA di-CH₂-AzI.

In accordance with another preferred alternative form of the invention, the $R^{14}$ and $R^{15}$ groups form, with the carbon atom to which they are connected, a cyclohexyl. In this case, $F^1$ and $F^2$ are identical and the CTA of formula (B) is advantageously the compound of formula:

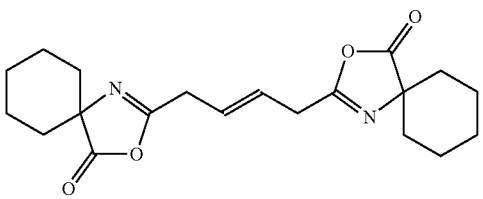 [SMILES: O=C1OC(C/C=C/CC2=NC3(CCCCC3)C(=O)O2)=NC12CCCCC2]

denoted below as CTA di-CH₂—HexAzl.

(c) Compound C of Formula (C1):

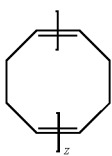
(C1)

The cyclic compound of formula (C1) generally comprises from 8 to 32 carbon atoms.

Preferably, it is chosen from the group formed by:
1,5-cyclooctadiene (denoted below by COD) formula:

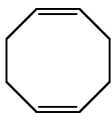

(corresponding to z=1)
and 1,5,9-cyclododecatriene (denoted below by CDT) composed of 12 carbon atoms of formula:

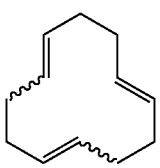 [SMILES: C1=CCC/C=C/CCC=CCC1]

(corresponding to z=2)
these 2 compounds being available commercially from Evonik Degussa and Arkema France.

(d) Compound C of Formula (C2):

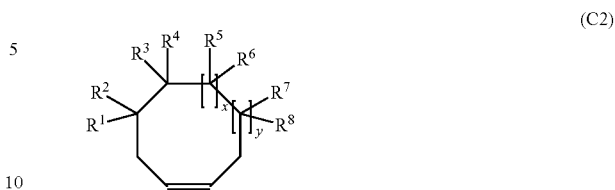
(C2)

The compound of formula (C2) generally comprises from 6 to 30 and preferably from 6 to 22 carbon atoms.

Preferably:
$R^1$, $R^2$, $R^3$, $R^4$, $R^5$, $R^6$, $R^7$ and $R^8$ represent a hydrogen atom or an alkyl radical comprising from 1 to 14 carbon atoms and more preferably from 1 to 8;
the integers x and y are within a range extending from 0 to 2, the sum x+y being within a range extending from 0 to 2.

According to an even more preferred alternative form:
x is equal to 1 and y is equal to 1 and/or
at most one of the groups taken from $R^1$, $R^2$, $R^3$, $R^4$, $R^5$, $R^6$, $R^7$ and $R^8$ is a $C_1$-$C_8$ alkyl radical and all the others represent a hydrogen atom.

The compound of formula (C2) is chosen in particular from:
cycloheptene, cyclooctene, cyclononene, cyclodecene, cycloundecene and cyclododecene,
5-epoxycyclooctene, of formula:

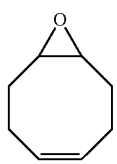

(available from Aldrich),
5-oxocyclooctene, of formula:

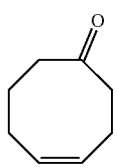

or also from a 5-alkylcyclooctene, of formula:

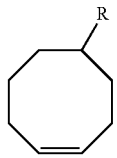

in which R is an alkyl radical comprising from 1 to 22 carbon atoms, preferably from 1 to 14 carbon atoms, R being, for example, the n-hexyl radical.

Among these compounds, cyclooctene is very particularly preferred.

(e) Compound C of Formula (C3):

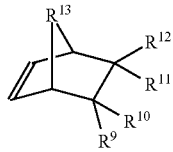

(C3)

The compound of formula (C3) generally comprises from 6 to 30 and preferably from 6 to 22 carbon atoms.

Preferably:
- $R^9$, $R^{10}$, $R^{11}$ and $R^{12}$ represent a hydrogen atom or an alkyl or alkoxycarbonyl radical comprising from 1 to 14 carbon atoms and more preferably still from 1 to 8;
- the $R^o$ radical included in the —$NR^o$— group, which is one of the meanings of $R^{13}$, is a linear radical comprising from 1 to 14 carbon atoms.

According to an even more preferred alternative form:
- at most one of the groups taken from $R^9$, $R^{10}$, $R^{11}$ and $R^{12}$ is a $C_1$-$C_8$ alkoxycarbonyl radical and all the others represent a hydrogen atom; and/or
- $R^{13}$ represents a —$CH_2$— radical or an oxygen atom.

The compound of formula (E) is chosen in particular from:

norbornene, of following formula:

norbornadiene, of following formula:

dicyclopentadiene, of following formula:

7-oxanorbornene, of following formula:

7-oxanorbornadiene, of following formula:

5-ethylidene-2-norbornene, of following formula:

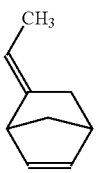

or methyl 5-norbornene-2-acetate, of following formula:

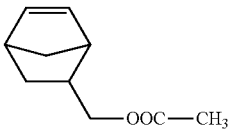

The compound of formula (C3) can also be chosen from the compounds of following formulae:

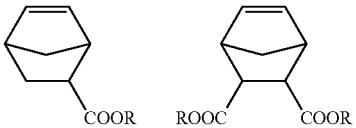

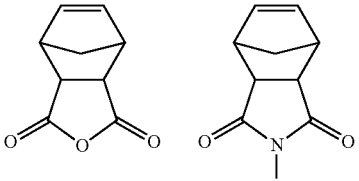

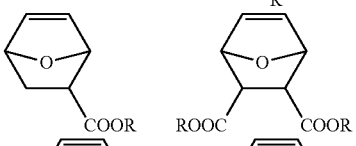

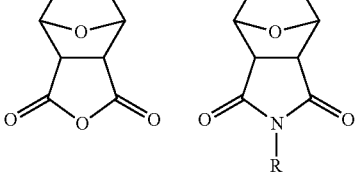

in which R is as defined above for the compound of formula (C2).

The compound of formula (C3) can also be chosen from the group formed by the addition products (or adducts) resulting from the Diels-Alder reaction using cyclopentadiene or furan as starting material, and also the compounds derived from norbornene, such as branched norbornenes, such as described in WO 2001/04173 (such as: norbornene isobornyl carboxylate, norbornene phenyl carboxylate, norbornene ethylhexyl carboxylate, norbornene phenoxyethyl carboxylate and alkyl norbornene dicarboxyimide, the alkyl generally comprising from 3 to 8 carbon atoms), and branched norbornenes, such as described in WO 2011/038057 (norbornene dicarboxylic anhydrides and optionally 7-oxanorbornene dicarboxylic anhydrides).

Preference is very particularly given, among the different compounds of formula (C3) cited, to norbornene, 7-oxanorbornene, methyl 5-norbornene-2-carboxylate, of formula:

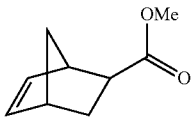 [SMILES: COC(=O)C1CC2C=CC1C2]

methyl 5-oxanorbornene-2-carboxylate, of formula:

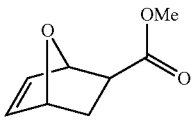

or dicyclopentadiene.

The stage of ring-opening metathesis polymerization (or ROMP) is generally carried out in the presence of at least one solvent, generally chosen from the group formed by the aqueous or organic solvents typically used in polymerization reactions and which are inert under the conditions of the polymerization, such as aromatic hydrocarbons, chlorinated hydrocarbons, ethers, aliphatic hydrocarbons, alcohols, water or their mixtures. A preferred solvent is chosen from the group formed by benzene, toluene, para-xylene, methylene chloride, dichloroethane, dichlorobenzene, chlorobenzene, tetrahydrofuran, diethyl ether, pentane, hexane, heptane, a mixture of liquid isoparaffins (for example Isopar®), methanol, ethanol, water or their mixtures. More preferably still, the solvent is chosen from the group formed by benzene, toluene, para-xylene, methylene chloride, 1,2-dichloroethane, dichlorobenzene, chlorobenzene, tetrahydrofuran, diethyl ether, pentane, hexane, heptane, methanol, ethanol or their mixtures. More particularly preferably still, the solvent is dichloromethane, 1,2-dichloroethane, toluene, heptane or a mixture of toluene and 1,2-dichloroethane. The solubility of the polymer formed during the polymerization reaction depends generally and mainly on the choice of the solvent, on the natures and the proportions of the comonomers and on the number-average molecular weight of the polymer obtained. It is also possible for the reaction to be carried out without solvent.

The process for the preparation of a hydrocarbon polymer according to the invention can additionally comprise at least one additional stage of hydrogenation of double bonds.

This stage is generally carried out by catalytic hydrogenation, most often under hydrogen pressure and in the presence of a hydrogenation catalyst, such as a catalyst of palladium supported by carbon (Pd/C). It more particularly makes it possible to form a saturated compound of formula (IH) from an unsaturated compound of formula (I') and in particular the saturated compounds corresponding to the compounds of formulae (II') and (III') from unsaturated compounds.

The invention also relates to the use, as adhesive, of the hydrocarbon polymer comprising two azlactone end groups, as defined above, as a mixture with an amino compound comprising at least two amine groups, for example chosen from diamines, triamines and higher homologues. The amounts of the hydrocarbon polymer and of the amino compound correspond to stoichiometric amounts, that is to say that the molar ratio of the number of azlactone groups to the number of amine groups ranges from 0.8 to 1.2, preferably from 0.9 to 1.1, indeed even is approximately 1.0.

In practice, the hydrocarbon polymer and the amino compound, used as curing agent, are advantageously each included in a component of a two-component composition which is made available to the user. The latter thus, at the time of use of the adhesive, mixes these 2 components, optionally under hot conditions, so as to obtain a liquid adhesive composition.

The invention also relates to a process for assembling two substrates by adhesive bonding, comprising:

coating, on at least one of the two substrates to be assembled, with a liquid adhesive composition obtained by mixing an amino compound comprising at least two amine groups with the hydrocarbon polymer comprising two azlactone end groups as is defined above; then actually bringing the two substrates into contact.

The liquid adhesive composition is either the adhesive composition comprising the said compound and the said polymer in the liquid state at ambient temperature or the molten adhesive composition under hot conditions. A person skilled in the art is in a position to proceed so that the adhesive composition used is in the liquid form at the time of its use.

The coating with the liquid adhesive composition is preferably carried out in the form of a layer with a thickness within a range from 0.3 to 5 mm, preferably from 1 to 3 mm, on at least one of the two surfaces which respectively belong to the two substrates to be assembled and which are intended to be brought into contact with one another along a faying surface. Actually bringing the two substrates into contact is then carried out along their faying surface.

Of course, the coating operation and the contacting operation have to be carried out within a compatible time interval, as is well known to a person skilled in the art, that is to say before the adhesive layer applied to the substrate loses its ability to attach, by adhesive bonding, this substrate to another substrate. In general, the polycondensation of the hydrocarbon polymer with the amino compound begins to take place during the coating operation and then continues to take place during the stage in which the two substrates are brought into contact.

The appropriate substrates are, for example, inorganic substrates, such as glass, ceramics, concrete, metals or alloys (such as aluminium alloys, steel, non-ferrous metals and galvanized metals); or else organic substrates, such as wood, plastics, such as PVC, polycarbonate, PMMA, polyethylene, polypropylene, polyesters or epoxy resins; substrates made of metal and composites coated with paint (as in the motor vehicle field).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 16.56/864, filed Jul. 19, 2016, are incorporated by reference herein.

The following examples are given purely by way of illustration of the invention and should not be interpreted in order to limit the scope thereof.

Examples 1 to 5 describe the preparation of polymers comprising 2 azlactone end groups by means of a ring-opening metathesis polymerization.

EXAMPLE 1

Polymerization of Cyclooctene (Compound C of Formula (C2)) In The Presence Of CTA $Azl_2$ Use is made of commercially available cyclooctene (denoted below as COE) and of CTA $Azl_2$ of formula:

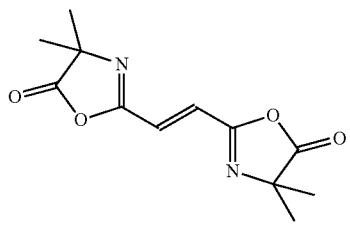 [SMILES: CC1(C)N=C(/C=C/C2=NC(C)(C)C(=O)O2)OC1=O]

The COE (10.8 mmol) and dry 1,2-dichloroethane (5 ml) are introduced into a 20 ml round-bottomed flask in which was also placed a Teflon®-coated magnetic stirring bar. The round-bottomed flask and its contents are subsequently placed under argon.

The compound CTA $Azl_2$ (0.216 mmol) is subsequently added with stirring to the round-bottomed flask via a syringe. The ratio of the reactants, expressed as number of moles: CTA $Azl_2$/COE, is 0.020.

The round-bottomed flask is then immersed in an oil bath at 60° C. and then the catalyst G2 defined above (5.4 µmol) in solution in 1,2-dichloroethane (2 ml) is immediately added using a hollow needle.

The reaction mixture becomes very viscous in the space of 10 minutes. The viscosity subsequently slowly decreases over the following hours.

After 8 hours, counting from the addition of the catalyst, the product present in the round-bottomed flask is extracted after evaporation of the solvent under vacuum. The product is then recovered in the form of a colourless solid powder, after precipitation from methanol, filtering and drying at 20° C. under vacuum, with a degree of conversion of the CTA of 50%.

The $^1H/^{13}C$ NMR analysis of the polymer obtained gives the following values:

$^1H$ NMR (CDCl$_3$, 400 MHz, 298 K) δ (ppm)=–repeat unit: 1.29 (8H*n), 1.96 (4H*n), 5.39 (2H*n); end group: 1.53 OC(O)C(CH3)2NCCH, 5.30 OC(O)C(CH3)2NCCHCH, 5.79OC(O)C(CH3)2NCCHCH.

$^{13}C$ NMR (CDCl$_3$, 100 MHz, 298 K) δ (ppm)=–repeat unit: 29.8 (4C*n), 33.7 (2C*n), 130.1 (2C*n); end group: 24.3 OC(O)C(CH3)2NCCH, 70.4 OC(O)C(CH3)2NCCH, 121.3OC(O)C(CH3)2NCCH, 161.4OC(O)C(CH3)2NCCH, 181.1OC(O)C(CH3)2NCCH;

These values confirm the following structure:

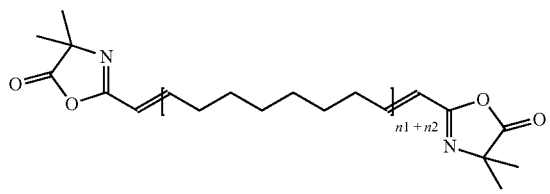

This structure is indeed covered by the formula (II') defined above.

The number-average molecular weight Mn, measured by NMR, is 6900 g/mol.

The polydispersity index, equal to the ratio Mw/Mn (measured by size exclusion chromatography with polystyrene standard), is 1.4.

EXAMPLE 2

Polymerization of COE in the Presence of CTA di-CH$_2$-Azl

Example 1 is repeated, CTA $Azl_2$ being replaced with CTA di-CH$_2$-Azl of formula:

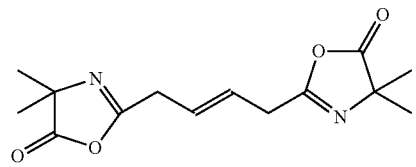 [SMILES: CC1(C)N=C(C/C=C/CC2=NC(C)(C)C(=O)O2)OC1=O]

A polymer in the form of a colourless solid powder is also recovered, but with a degree of conversion of the CTA of 100%, the $^1H/^{13}C$ NMR analysis of which gives the following values:

$^1H$ NMR (CDCl$_3$, 400 MHz, 298 K) δ (ppm)=–repeat unit: 1.29 (8H*n), 1.96 (4H*n), 5.39 (2H*n); end group: 1.42 (s, 12H) OC(O)C(CH3)2NCCH2CH, 3.17 (m, 4H) OC(O)C(CH3)2NCCH2CH.

$^{13}C$ NMR (CDCl$_3$, 100 MHz, 298 K) δ (ppm)=–repeat unit: 29.8 (4C*n), 33.7 (2C*n), 130.1 (2C*n); end group: 25.0 OC(O)C(CH3)2NCCH2CH, 40.6 OC(O)C(CH3)2NCCH2CH, 57.4OC(O)C(CH3)2NCCH2CH, 131.2 OC(O)C(CH3)2NCCH2CH, 173.1OC(O)C(CH3)2NCCH2CH, 176.0 OC(O)C(CH3)2NCCH2CH;

These values confirm the structure below, also covered by the formula (II'):

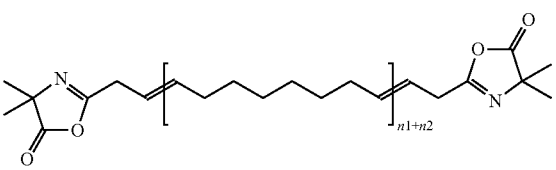

The number-average molecular weight Mn and the polydispersity index are respectively 6000 g/mol and 1.3.

EXAMPLE 3

Polymerization of 1,5,9-cyclododecatriene (Compound C of Formula (C1)) and of Norbornene (Compound C of Formula (C3)) in the Presence of CTA di-$CH_2$-Azl Example 2 is repeated, the 10.8 mmol of COE being replaced with a mixture of 5.4 mmol of 1,5,9-cyclododecatriene (also denoted CDT) and of 5.4 mmol of norbornene, of formula:

available from Sigma-Aldrich.

The ratio of the reactants, expressed as number of moles: CTA di-$CH_2$-Azl/(CDT+norbornene), is 0.020.

A polymer in the form of a colourless viscous liquid is also recovered, with a degree of conversion of the CTA of 100%, the $^1H/^{13}C$ NMR analysis of which gives the following values:

$^1$H NMR: δ (ppm) repeat unit trans: 1.08 (2H*n), 1.39 (4H*n), 2.07 (4H*n), 2.47 (2H*n trans), 5.24-5.44 (4H*n trans), cis: 1.82-1.91 (6H*n), 2.07 (4H*n), 2.82 (2H*n cis), 5.24-5.44 (4H*n cis), end group=1.42 (s, 12H) OC(O)C(CH3)2NCCH2CH, 3.17 (m, 4H) OC(O)C(CH3)2NCCH2CH.

$^{13}$C NMR: δ (ppm) repeat unit: 27.4, 33.1, 42.1, 43.4, 130.3, 133.1, end group=25.0 OC(O)C(CH3)2NCCH2CH, 40.6OC(O)C(CH3)2NCCH2CH, 57.4 OC(O)C(CH3)2NCCH2CH, 131.2OC(O)C(CH3)2NCCH2CH, 173.1OC(O)C(CH3)2NCCH2CH, 176.0OC(O)C(CH3)2NCCH2CH.

These values confirm the structure below:

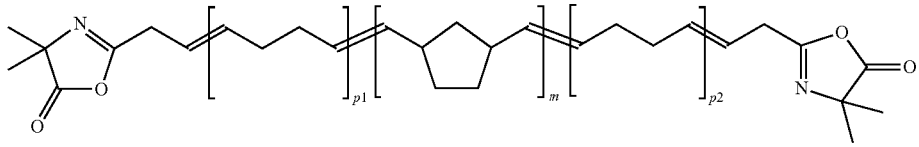

This structure is indeed covered by the formula (III') defined above.

The number-average molecular weight Mn and the polydispersity index are respectively 6900 g/mol and 1.5.

EXAMPLE 4

Polymerization pf COE in the Presence of CTA di-$CH_2$-HexAzl

Example 1 is repeated, CTA $Azl_2$ being replaced with CTA di-$CH_2$-HexAzl of formula:

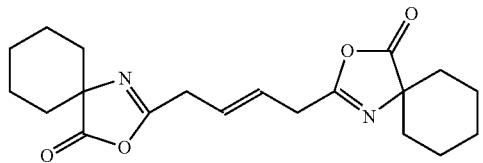 [SMILES: O=C1OC(C/C=C/CC2=NC3(CCCCC3)C(=O)O2)=NC12CCCCC2]

A polymer in the form of a colourless solid powder is also recovered, but with a degree of conversion of the CTA of 100%, the $^1$H/$^{13}$C NMR analysis of which gives the following values:

$^1$H NMR (CDCl$_3$, 400 MHz, 298 K) δ (ppm)=–repeat unit: 1.29 (8H*n), 1.96 (4H*n), 5.39 (2H*n); end group 1.42-1.62 (m, 20H) OC(O)C(C5H10)NCCH2CH, 3.25 (m, 4H) OC(O)C(C5H10)NCCH2CH, 5.65 (s, 2H) OC(O)C(C5H10)NCCH2CH;

$^{13}$C NMR (CDCl$_3$, 100 MHz, 298 K) δ (ppm)=–repeat unit: 29.8 (4C*n), 33.7 (2C*n), 130.1 (2C*n); end group: 20.7, 24.45, 32.8 OC(O)C(C5H10)NCCH2CH, 29.9OC(O)C(C5H10)NCCH2CH, 68.2 OC(O)C(C5H10)NCCH2CH, 120.5OC(O)C(C5H10)NCCH2CH, 162.4 OC(O)C(C5H10)NCCH2CH, 182.6OC(O)C(C5H10)NCCH2CH;

These values confirm the structure below:

This structure is indeed covered by the formula (II') defined above.

The number-average molecular weight Mn and the polydispersity index are respectively 5500 g/mol and 1.3.

EXAMPLE 5

Polymerization of CDT and Norbornene in the Presence of CTA di-CH$_2$-HexAzl

Example 3 is repeated, CTA di-CH$_2$-Azl being replaced with CTA di-CH$_2$-HexAzl.

A copolymer in the form of a colourless viscous liquid is also obtained, with a degree of conversion of the CTA of 100%, the $^1$H/$^{13}$C NMR analysis of which gives the following values:

$^1$H NMR: δ (ppm) repeat unit trans: 1.08 (2H*n), 1.39 (4H*n), 2.07 (4H*n), 2.47 (2H*n trans), 5.24-5.44 (4H*n trans), cis: 1.82-1.91 (6H*n), 2.07 (4H*n), 2.82 (2H*n cis), 5.24-5.44 (4H*n cis), end group=1.42-1.62 (m, 20H) OC(O)C(C5H10)NCCH2CH, 3.25 (m, 4H) OC(O)C(C5H10)NCCH2CH;

$^{13}$C NMR: δ (ppm) repeat unit: 27.4, 33.1, 42.1, 43.4, 130.3, 133.1, end group=20.7, 24.45, 32.8OC(O)C(C5H10)NCCH2CH, 29.9 OC(O)C(C5H10)NCCH2CH, 68.3OC(O)C(C5H10)NCCH2CH, 131.7 OC(O)C(C5H10)NCCH2CH, 162.2OC(O)C(C5H10)NCCH2CH, 181.0 OC(O)C(C5H10)NCCH2CH;

These values confirm the structure:

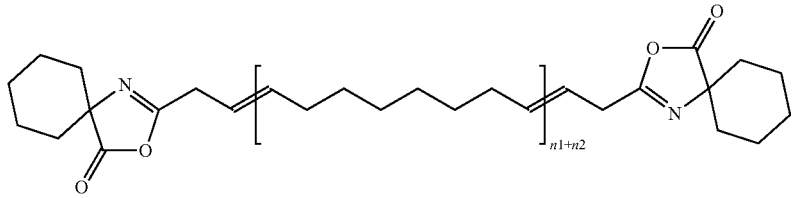

This structure is indeed covered by the formula (III') defined above.

The number-average molecular weight Mn and the polydispersity index are respectively 6600 g/mol and 1.6.

EXAMPLE 6

Synthesis of Polyamide from the Unsaturated Polyolefin Comprising Two Azlactone End Groups of Example 5

A stoichiometric mixture in methyl ethyl ketone of the polyolefin comprising two azlactone groups obtained in Example 5 with a primary diamine of polyether diamine type (Jeffamine EDR 176, Huntsman) was left at ambient temperature, until complete disappearance of the infrared band characteristic of the azlactone groups (at 1815 cm$^{-1}$) and appearance of the bands characteristic of the amide bond (bands at 1550 and 1530 cm$^{-1}$). The duration of the reaction is approximately 1 hour.

The product thus synthesized resulted in the formation of polyamide which, appropriately formulated, made it possible to obtain adhesive properties.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Hydrocarbon polymer comprising two azlactone end groups, the said hydrocarbon polymer having the formula (I):

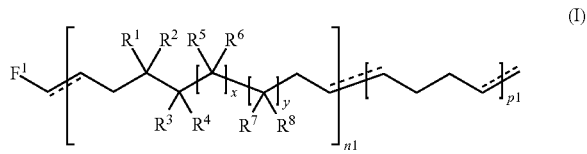

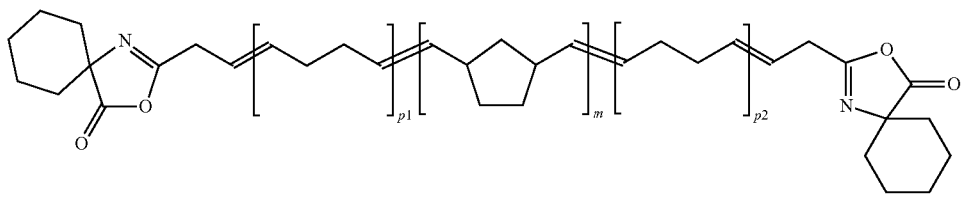

-continued

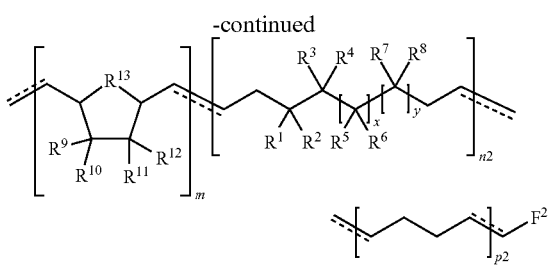

in which:

F¹ represents a radical of formula (IIa) and F² represents a radical of formula (IIb):

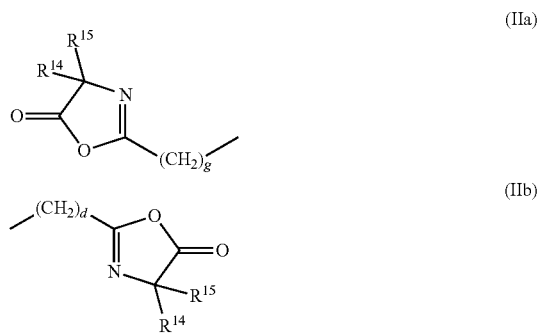

in which:

g and d, which are identical or different, represent an integer equal to 0, 1, 2 or 3;

$R^{14}$ and $R^{15}$, which are identical or different, represent a hydrogen atom or an aromatic or linear or branched aliphatic hydrocarbon group comprising from 1 to 20 carbon atoms which can be interrupted by one or more oxygen or sulphur atoms; in addition, the $R^{14}$ and $R^{15}$ groups can form, with the carbon atom to which they are connected, a hydrocarbon ring comprising from 4 to 10 ring members and optionally one or more heteroatoms chosen from oxygen and sulphur;

each carbon—carbon bond of the main chain of the polymer, denoted ------ , represents a double bond or a single bond, in accordance with the valency rules of organic chemistry;

$R^1$, $R^2$, $R^3$, $R^4$, $R^5$, $R^6$, $R^7$ and $R^8$, which are identical or different, represent:

a hydrogen or halogen atom; or a radical comprising from 1 to 22 carbon atoms chosen from alkyl, alkenyl, alkoxycarbonyl, alkenyloxycarbonyl, alkylcarbonyloxy or alkenylcarbonyloxy, it being possible for the hydrocarbon chain of the said radical to be optionally interrupted by at least one oxygen atom or one sulphur atom; in addition:

at least one of the $R^1$ to $R^8$ groups can form, with at least one other of the $R^1$ to $R^8$ groups and with the carbon atom or atoms to which the said groups are connected, a saturated or unsaturated hydrocarbon ring or heterocycle which is optionally substituted and which comprises from 3 to 10 ring members; and at least one of the pairs ($R^1$, $R^2$), ($R^3$, $R^4$), ($R^5$, $R^6$) and ($R^7$, $R^8$) can form, with the carbon atom to which the said pair is connected, a carbonyl C=O group or a group of 2 carbon atoms connected by a double bond: C=C, the other carbon atom of which carries 2 substituents chosen from a hydrogen atom or a $C_1$-$C_4$ alkyl radical;

x and y are integers, which are identical or different, within a range extending from 0 to 6, the sum x+y being within a range extending from 0 to 6;

$R^9$, $R^{10}$, $R^{11}$ and $R^{12}$, which are identical or different, represent:

a hydrogen or halogen atom; or a radical comprising from 1 to 22 carbon atoms which is chosen from alkyl, alkenyl, alkoxycarbonyl, alkenyloxycarbonyl, alkylcarbonyloxy, alkenylcarbonyloxy or alkylcarbonyloxyalkyl, it being possible for the hydrocarbon chain of the said radical to be optionally interrupted by at least one oxygen atom or one sulphur atom; in addition:

at least one of the $R^9$ to $R^{12}$ groups can form, with at least one other of the $R^9$ to $R^{12}$ groups and with the carbon atom or atoms to which the said groups are connected, a saturated or unsaturated hydrocarbon ring or heterocycle which is optionally substituted and which comprises from 3 to 10 ring members; and at least one of the pairs ($R^9$, $R^{10}$) and ($R^{11}$, $R^{12}$) can form, with the carbon atom to which the said pair is connected, a group of 2 carbon atoms connected by a double bond: C=C, the other carbon atom of which carries 2 substituents chosen from a hydrogen atom or a $C_1$-$C_4$ alkyl radical; and the carbon atom carrying one of the groups of the pair ($R^9$, $R^{10}$) can be connected to the carbon atom carrying one of the groups of the pair ($R^{11}$, $R^{12}$) by a double bond, it being understood that, in accordance with the valency rules, just one of the groups of each of these 2 pairs is then present;

$R^{13}$ represents:

an oxygen or sulphur atom, or a divalent —$CH_2$—, —C(=O)— or —$NR^0$— radical in which $R^0$ is an alkyl or alkenyl radical comprising from 1 to 22 carbon atoms;

n1 and n2, which are identical or different, are each an integer or equal to 0, the sum of which is denoted by n;

m is an integer or equal to 0;

p1 and p2, which are identical or different, are each an integer or equal to 0, the sum p1+p2 of which adheres to the equation:

$$p1+p2=q \times (z+1)$$

in which:

q is an integer or equal to 0; and z is an integer ranging from 1 to 5; and n1, n2, m, p1 and p2 additionally being such that the number-average molecular weight Mn of the polymer of formula (I) is within a range extending from 400 to 100 000 g/mol and its polydispersity index is within a range extending from 1.0 to 3.0.

2. Hydrocarbon polymer according to claim 1, characterized in that:

the $R^{14}$ and $R^{15}$ radicals represent a $C_1$-$C_4$ alkyl radical or else form, with the carbon atom to which they are connected, a cyclohexyl radical;

g and d represent 0 or 1;

$R^1$, $R^2$, $R^3$, $R^4$, $R^5$, $R^6$, $R^7$ and $R^8$ represent a hydrogen atom or an alkyl radical comprising from 1 to 14 carbon atoms;

x and y are within a range extending from 0 to 2, the sum x+y being within a range extending from 0 to 2;

$R^9$, $R^{10}$, $R^{11}$ and $R^{12}$ represent a hydrogen atom or a radical, the hydrocarbon part of which comprises from 1 to 14 carbon atoms;

$R^{13}$ represents the divalent —$CH_2$— radical;

z is an integer equal to 1 or 2; and the number-average molecular weight Mn is within a range extending from 3000 to 50 000 g/mol.

3. Hydrocarbon polymer according to claim 1, characterized in that:

when m is non-zero, when p1 and p2 are non-zero and when n1 and n2 are each equal to 0, then the ratio:

m/(p1+p2+m)

is within the interval ranging from 30 to 70%; or when m is equal to 0, when p1 and p2 are non-zero and when the sum n1 +n2 is non-zero, then at least one of the $R^1$, $R^2$, $R^3$, $R^4$, $R^5$, $R^6$, $R^7$ and $R^8$ groups is other than a hydrogen atom, and the ratio:

(n1 +n2)/(p1 +p2+n1+n2)

is within the interval ranging from 30 to 70%; or when m is other than 0, when p1 and p2 are each equal to 0, when the sum n1+n2 is non-zero and when each of the $R^1$, $R^2$, $R^3$, $R^4$, $R^5$, $R^6$, $R^7$ and $R^8$ groups is a hydrogen atom, then the ratio:

m/(m +n1+n2)

is within the interval ranging from 30 to 70%; or when m is non-zero, when p1 and p2 are non-zero, when the sum n1+n2 is non-zero and when each of the $R^1$, $R^2$, $R^3$, $R^4$, $R^5$, $R^6$, $R^7$ and $R^8$ groups is a hydrogen atom, then the ratio:

m/(p1+p2+n1+n2+m)

is within the interval ranging from 30 to 70%; or when m is non-zero, when p1 and p2 are non-zero, when the sum n1+n2 is non-zero and when at least one of the $R^1$, $R^2$, $R^3$, $R^4$, $R^5$, $R^6$, $R^7$ and $R^8$ groups is other than a hydrogen atom, then the ratio:

(m+n1+n2)/(p1+p2+n1+n2+m)

is within the interval ranging from 30 to 70%.

4. Hydrocarbon polymer according to claim 1, characterized in that it has the following formula (I'):

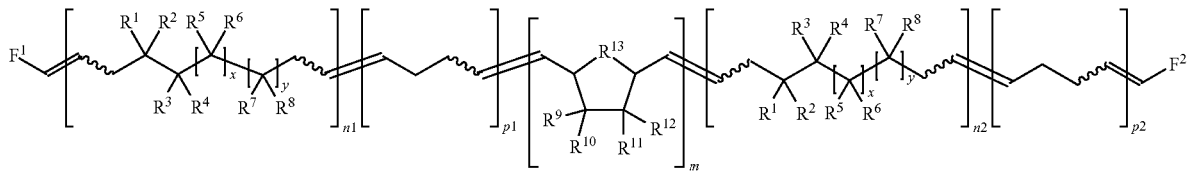

in which the ⁓ bond is a bond geometrically oriented on one side or the other with respect to the double bond.

5. Hydrocarbon polymer according to claim 1, characterized in that it has the following formula (II'):

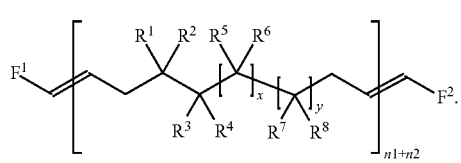

6. Hydrocarbon polymer according to claim 1, characterized in that it has the following formula (III'):

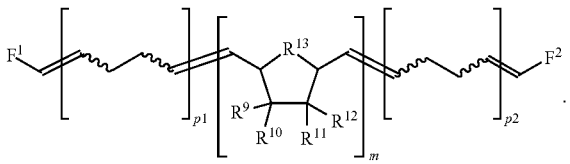

7. Process for the preparation of a hydrocarbon polymer comprising two azlactone end groups of formula (I) as defined in claim 1, the said process comprising at least one ring-opening metathesis polymerization reaction, in the presence:

(a) of a metathesis catalyst;

(b) of a chain transfer agent (or CTA) comprising 2 azlactone groups, of following formula (B):

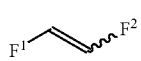

in which the ⁓ bond is a bond geometrically oriented on one side or the other with respect to the double bond; and (c) of at least one compound C chosen from:

the compound of formula (C1):

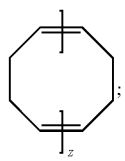

the compound of formula (C2):

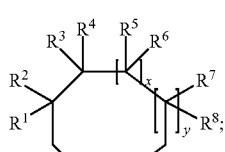

and the compound of formula (C3):

(C3)

the said polymerization reaction being carried out:
  for a time ranging from 2 to 24 hours and at a temperature within an interval from 20 to 70° C.; and
  with a ratio r, equal to the ratio of the number of moles of the said CTA to the total number of moles of the compound C, within an interval ranging from 0.0010 to 1.0.

8. An adhesive comprising the hydrocarbon polymer as defined in claim 1, as a mixture in stoichiometric amounts with an amino compound comprising at least two amine groups.

9. Process for assembling two substrates by adhesive bonding, comprising:
  coating, on at least one of the two substrates to be assembled, with a liquid adhesive composition obtained by mixing an amino compound comprising at least two amine groups with the hydrocarbon polymer as defined in claim 1; then
  actually bringing the two substrates into contact.

* * * * *